(12) United States Patent
Distefano

(10) Patent No.: US 9,757,222 B2
(45) Date of Patent: Sep. 12, 2017

(54) SNAPBACK CARD IMPLANT PACKAGE

(71) Applicant: Howmedica Osteonics Corp., Mahwah, NJ (US)

(72) Inventor: Nicole Distefano, Westwood, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 14/867,728

(22) Filed: Sep. 28, 2015

(65) Prior Publication Data

US 2017/0086958 A1    Mar. 30, 2017

(51) Int. Cl.
| | |
|---|---|
| *B65D 83/10* | (2006.01) |
| *A61F 2/00* | (2006.01) |
| *B65D 77/30* | (2006.01) |
| *B65B 61/20* | (2006.01) |

(52) U.S. Cl.
CPC ............ *A61F 2/0095* (2013.01); *B65B 61/20* (2013.01); *B65D 77/30* (2013.01)

(58) Field of Classification Search
CPC ....... A61F 2/0095; B65B 61/20; B65D 77/30; B65D 83/10
USPC ....... 206/363, 364, 210, 223, 472, 478, 565, 206/583, 438, 63.5, 387.13, 387.11, 477, 206/497, 486, 747, 745, 749
See application file for complete search history.

(56) References Cited

U.S. PATENT DOCUMENTS

| | | |
|---|---|---|
| 4,111,302 A | 9/1978 | Roth |
| 5,165,540 A * | 11/1992 | Forney ................. A61M 25/002 |
| | | 206/363 |
| 5,193,679 A | 3/1993 | White |
| 5,284,244 A | 2/1994 | O'Toole et al. |
| 5,379,895 A | 1/1995 | Foslien |
| 5,386,908 A | 2/1995 | Sinn |
| 5,474,179 A | 12/1995 | Iosif et al. |
| 5,678,695 A | 10/1997 | Ridgeway et al. |
| 5,893,462 A | 4/1999 | Ridgeway |

(Continued)

OTHER PUBLICATIONS

Verizon Wireless return box, "Instructions on how to pack product for return", Front view, 1 page, Image was captured on Sep. 25, 2015.

(Continued)

*Primary Examiner* — Jacob K Ackun
*Assistant Examiner* — Rafael Ortiz
(74) *Attorney, Agent, or Firm* — Lerner, David, Littenberg, Krumholz & Mentlik, LLP

(57) ABSTRACT

A product package includes a first member and a second member arrangeable in an unpackaged state and a packaged state. The package has a flexible member attached to the first and second members which assists in securing an implant to the first member. The flexible member is slack when the package is in the unpackaged state and is taut in the packaged state. The first member is coupled to the second member by a connector in the packaged state with the product secured between the first member and the flexible member. The flexible member is externally exposed when the package is in the packaged state. The package can also include an insert coupled to the first member to assist in securing the product in the package. The flexible member can have a pull tab forming a frangible connection with the flexible member to open the package. The flexible member may form a sterile barrier around the product.

14 Claims, 8 Drawing Sheets

(56) References Cited

U.S. PATENT DOCUMENTS

| | | | |
|---|---|---|---|
| 6,010,003 A * | 1/2000 | Wilkinson | B65D 5/5028 206/478 |
| 6,059,111 A | 5/2000 | Davila et al. | |
| 6,161,695 A | 12/2000 | Nicolais | |
| 6,183,467 B1 | 2/2001 | Shapeton et al. | |
| 6,223,901 B1 | 5/2001 | Lofgren et al. | |
| 6,358,241 B1 | 3/2002 | Shapeton et al. | |
| 6,467,624 B1 | 10/2002 | Lofgren et al. | |
| 6,675,973 B1 | 1/2004 | McDonald et al. | |
| 6,874,629 B1 | 4/2005 | Wortrich | |
| 6,889,839 B1 * | 5/2005 | Rosten | B65D 81/075 206/363 |
| 6,915,901 B2 * | 7/2005 | Feinberg | A61B 17/00491 206/363 |
| 6,920,981 B2 | 7/2005 | Lofgren et al. | |
| 6,942,101 B2 | 9/2005 | Lofgren et al. | |
| 7,290,662 B2 | 11/2007 | Lofgren et al. | |
| 7,296,681 B2 | 11/2007 | McDonald et al. | |
| 7,316,318 B1 | 1/2008 | Rosten et al. | |
| 7,669,716 B2 | 3/2010 | Lightner et al. | |
| 7,699,162 B2 | 4/2010 | Tokarski et al. | |
| 7,731,032 B2 | 6/2010 | McDonald et al. | |
| 8,028,838 B2 | 10/2011 | Mcdonald et al. | |
| 8,038,006 B2 | 10/2011 | Berry et al. | |
| 8,096,420 B2 | 1/2012 | Marhsall et al. | |
| 8,146,741 B2 | 4/2012 | Matsuoka et al. | |
| 8,230,996 B1 | 7/2012 | Cummings et al. | |
| 8,499,937 B2 | 8/2013 | McDonald et al. | |
| 8,567,603 B2 | 10/2013 | Liccardo et al. | |
| 8,966,867 B2 | 3/2015 | Liccardo et al. | |
| 9,067,722 B2 | 6/2015 | Mcdonald et al. | |
| 2004/0178113 A1 | 9/2004 | Lofgren et al. | |
| 2005/0252825 A1 | 11/2005 | Lofgren et al. | |
| 2006/0000743 A1 | 1/2006 | Lofgren et al. | |
| 2006/0138018 A1 | 6/2006 | McDonald et al. | |
| 2007/0295620 A1 | 12/2007 | Collet et al. | |
| 2010/0133133 A1 | 6/2010 | Hamas | |
| 2012/0191203 A1 * | 7/2012 | Liccardo | A61F 2/0095 623/19.11 |
| 2012/0193405 A1 | 8/2012 | McDonald et al. | |
| 2014/0076769 A1 * | 3/2014 | McDonald | B65B 55/20 206/583 |
| 2014/0183097 A1 | 7/2014 | LeRoy et al. | |
| 2016/0016714 A1 * | 1/2016 | Fenech, III | B65D 75/5833 206/459.1 |
| 2016/0148543 A1 * | 5/2016 | Spreck | B05D 3/12 206/459.5 |

OTHER PUBLICATIONS

Verizon Wireless return box, "Instructions on how to pack product for return", view No. 1 from the return box, 1 page, Image was captured on Sep. 25, 2015.

Verizon Wireless return box, "Instructions on how to pack product for return", view No. 2 from the return box, 1 page, Image was captured on Sep. 25, 2015.

Verizon Wireless return box, "Instructions on how to pack product for return", closer front view, 1 page, Image was captured on Sep. 25, 2015.

Verizon Wireless return box, "Instructions on how to pack product for return", view No. 3 from the return box, 1 page, Image was captured on Sep. 25, 2015.

Barger™ Placon's Medical Specialists Packaging Brochure, Jul. 2015.

Korrvu® Packaging Retention Box Packing Instructions, Jan. 2014.

Korrvu® Retention Packaging Packing Instructions, Jan. 2011.

Korrvu® Suspension Packaging Notebook Computer Packing Instructions, Jan. 2012.

* cited by examiner

SNAPBACK CARD IMPLANT PACKAGE

BACKGROUND OF THE INVENTION

The present invention relates to the packaging of implants and more particularly to the packaging of implants for secure shipment and storage, as well as ease of use in the operating arena. Some conventional implant packages rely on a void-filling approach to protect their contents. The void-filling approach entails stabilizing the contents within a rigid plastic package with a variety of foams and padding materials. The foam and padding materials essentially fill the void between the implant and the inner surfaces of the rigid plastic package. The rigid plastic package is then sealed with lidstock material.

The void-filling approach requires the use of multiple foam components which are usually bulky and generate a considerable volume of package waste. Additionally, implants packed in foam can be difficult to remove without premature or accidental exposure to biological material on surgical gloves since the foams are intended to provide a tight fit to cushion the package and the implant. The void-filling approach also requires some manual processes, which are prone to error and typically result in a long packaging process time. Once the sterile barrier of a package has been compromised, the medical implant contained within that package cannot be used in surgery. Indeed, if a medical implant has been contaminated and the physician has no back-up medical implant on hand, surgery could be delayed.

Another type of implant package is a clamshell configuration. The clamshell includes two rigid plastic pieces hinged at one end. An implant is placed on one of the rigid pieces and the other rigid piece is closed over the implant such that the two rigid pieces form a container for the implant. However, such clamshell packages are often difficult to open, particularly when the user is wearing surgical gloves. Thus, a need exists for an improved product package.

BRIEF SUMMARY OF THE INVENTION

One aspect of the disclosure desirably includes a product package having first and second members arrangeable in an unpackaged state and a packaged state in which a distal side of the first member is connected to a second side of the second member. The package may have a flexible member which at least assists in holding a product between the proximal side of the first member and the flexible member. The flexible member can be coupled to the proximal side of the first member and the first side of the second member.

The first and second members can be rigid and may be coupled to one another by a living hinge such that the proximal side of the first member and the first side of the second member are coplanar when the product package is in the unpackaged state. A connector having male and female elements can be formed on the distal side of the first member and the second side of the second member to assist in securing the package in the packaged state.

The flexible member may have a pull tab forming a frangible connection to the flexible member to allow the package to be opened. The flexible member can be lax when the product package is in the unpackaged state and taut in the packed state. The flexible member may be elastically deformed when the product package is in the packaged state.

The product package can also include an insert coupled to the proximal side of the first member. The insert can have a ridge to at least partially secure a product to the insert. The product may be a medical device.

A method of packaging a product according to one aspect of the disclosure desirably includes placing a product on a proximal side of a first member, securing a flexible member to the proximal side of the first member and a first side of a second member, and transitioning the package from an unpackaged state to a packaged state such that the second side of the second member is adjacent a distal side of the first member and the product is between the proximal side of the first member and the flexible member.

The method may also include engaging male and female elements of a connector formed on opposing surfaces of the first and second members to assist in holding the product package in the packaged state. The method can include tautening and/or elastically deforming the flexible member as the product package is transitioned from the unpackaged to the packaged state.

The method can also include securing an insert between the flexible member and the proximal side of the first member to receive the product. The transitioning step may include rotating one of the first and second members about a living hinge coupling the first and second members to each other.

DETAILED DESCRIPTION

Figure 1:
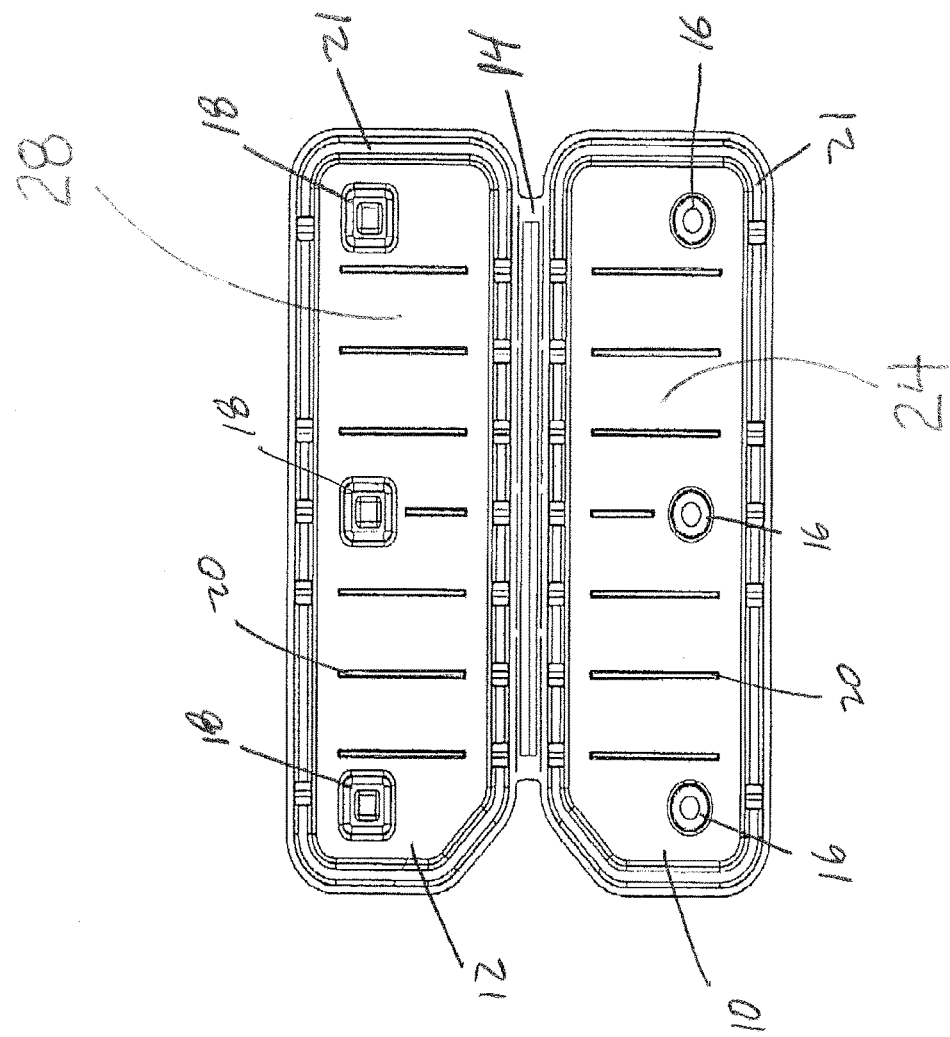
FIG. 1 is a top view of first and second members in accordance with one embodiment of the present disclosure.
Figure 2:
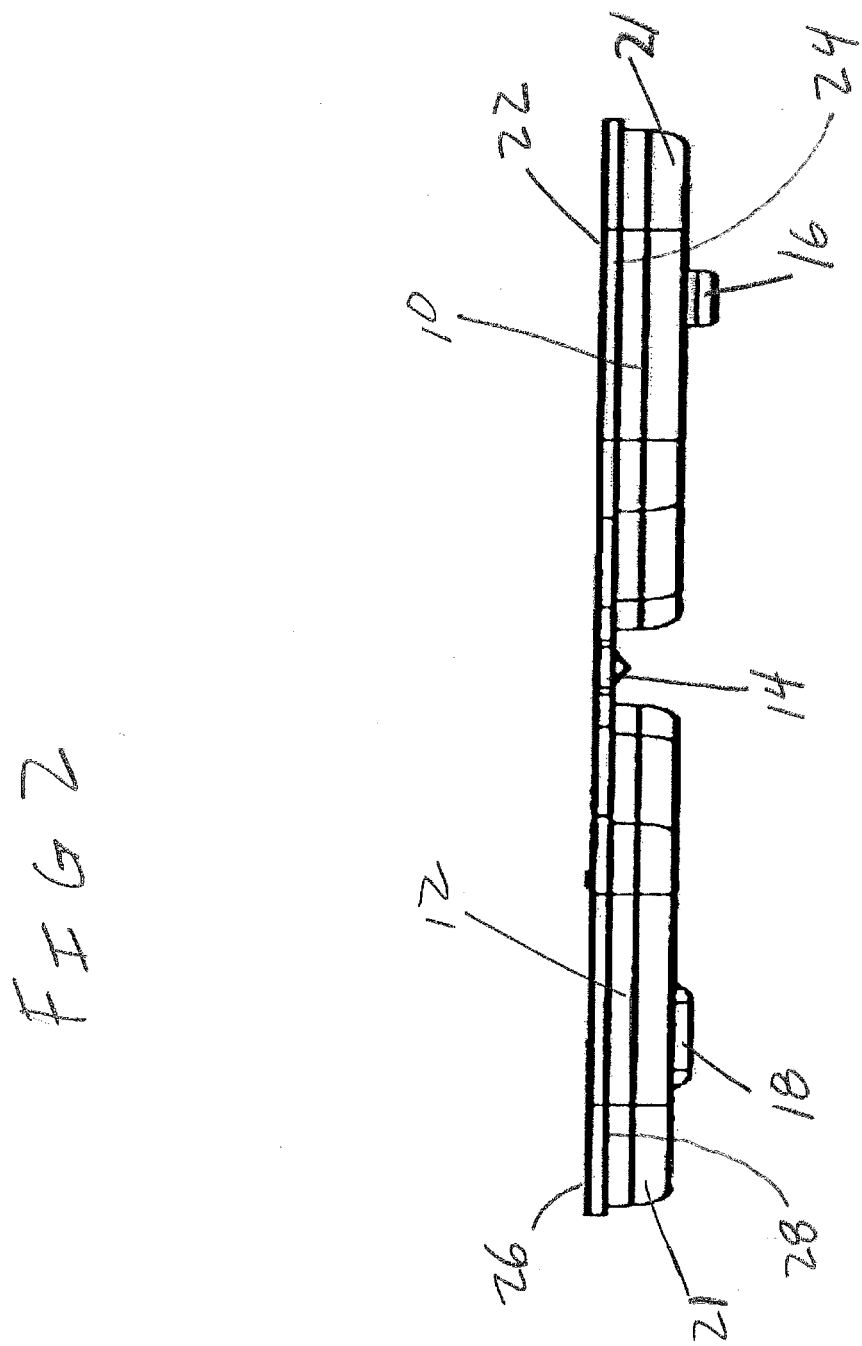
FIG. 2 illustrates a side view of the first and second members of FIG. 1

With reference to FIGS. 1-7, the present disclosure relates to a package for holding any suitable medical item such as an orthopedic medical implant. The package includes a first member 10 and a second member 12 as shown in FIG. 1 which depicts the package in a first, unpackaged state. The first and second members 10, 12 are connected by a web 14 in FIG. 1. The web 14 could be a living hinge which allows relative motion between the first and second members 10, 12. In other embodiments, there is no web and the members are merely in the vicinity of one another in the first state. As best seen in FIG. 2, the first member 10 has a proximal side 22 and a distal side 24. The second member 12 has a first side 26 and a second side 28. The proximal side 22 of the first member and the first side 26 of the second member 12 can be co-planar when the package is in the first state.

The first member 10 includes male connectors 16 which are designed to engage female connectors 18 on the second member 12 when the package is in a second, packaged state.

The connectors provide an interference fit with each other to at least partially secure the package in the second state. Of course, the male and female elements of the connector could be on the either of the members. Further, the connector may be any suitable connector consistent with the objective of the invention, including Velcro, permanent or temporary adhesives, etc.

The members 10, 12 optionally include reinforcing ridges 20. The members 10, 12 also include a border 21 which stands proud of the distal side 24 surface and the second side 28 surface. The connectors 16, 18 preferably extend away from the distal side and second side surfaces of the members further than the border 21 to allow the connectors to engage one another as best seen in FIG. 2. The members 10, 12 are preferably made from a rigid material PETG Copolyester manufactured by Pacur (Oshkosh, Wis.), although other materials are also contemplated.

Figure 3:
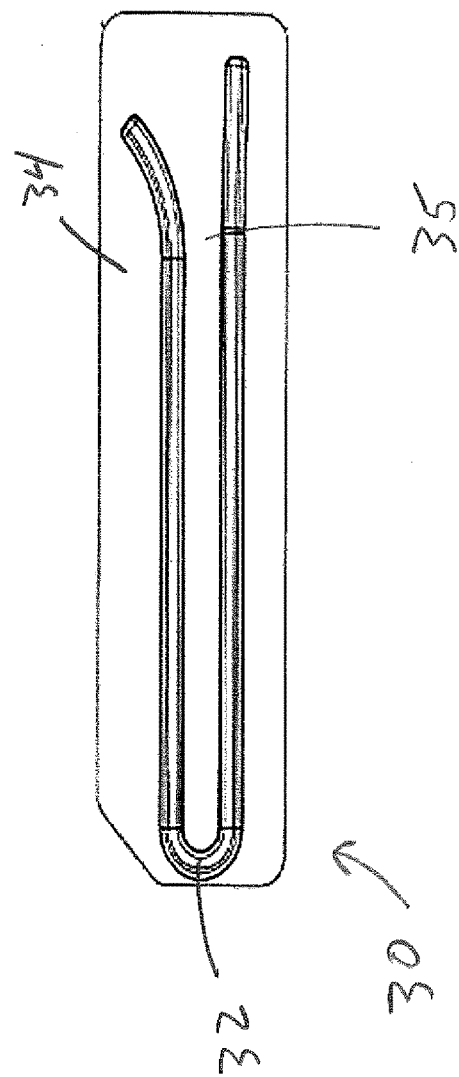
FIG. 3 illustrates a top view of an insert in accordance with one embodiment of the present disclosure.
Figure 6:
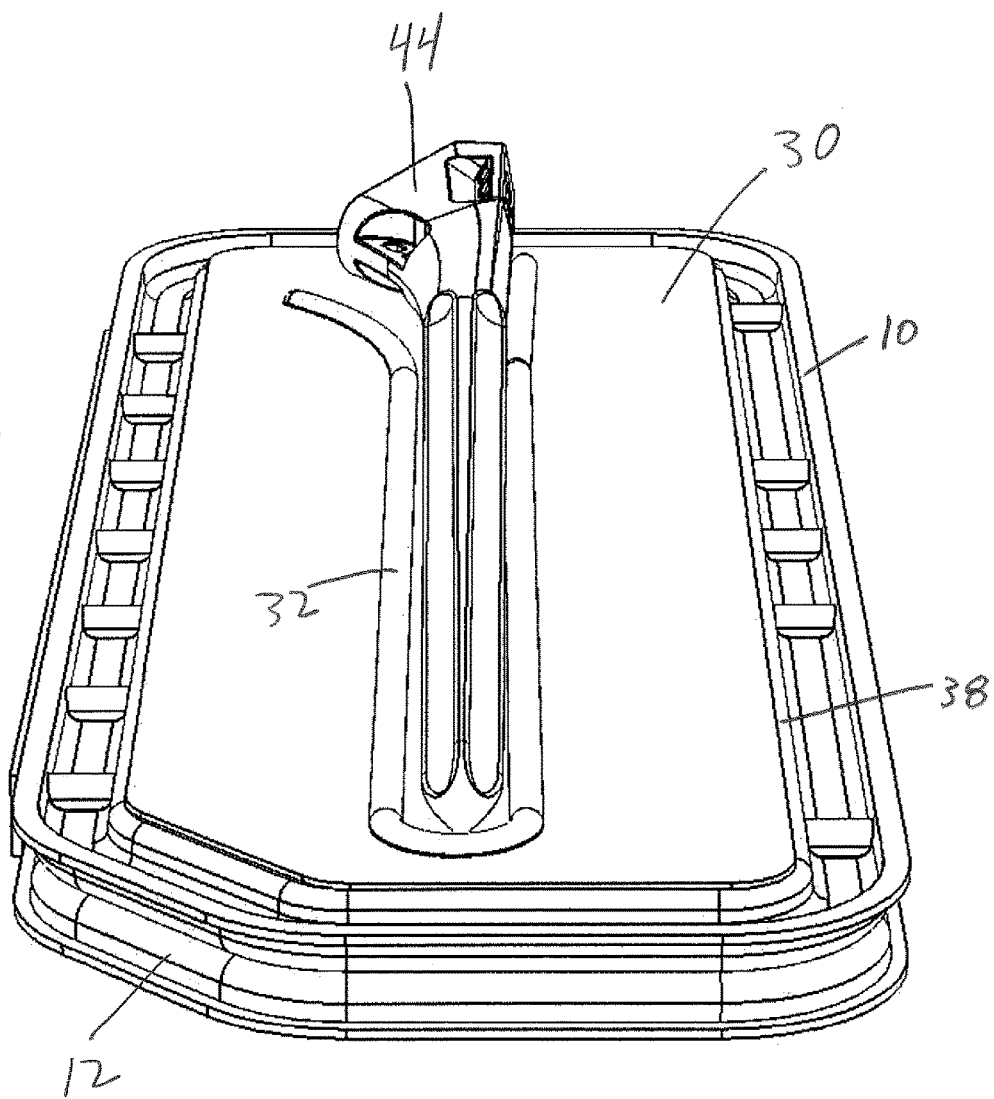
FIG. 6 illustrates a perspective view of the product package of FIG. 4 in a second state with a product in the package.

The product package can include an insert 30 as shown in FIG. 3. The insert 30 includes a ridge 32 standing proud of a surface 34. The ridge 32 defines a receiving area 35 which assists in securing the implant in the package. The receiving area 35 can be adapted to the outline of any product or implant which will be contained in the package. The insert 30 can be placed on the proximal side 22 of the first member 10 and separate the implant from the first member 10 as best seen in FIG. 6. The insert 30 is preferably manufactured from a softer material than that of the first member (e.g. Thermoplastic polyurethane) such that the insert can prevent abrasion of the implant from the first member. The insert 30 can also include pilot holes (not shown) adapted to receive studs on the proximal side of the first member (not shown) to align and maintain the position of the insert on the proximal side of the first member. The insert 30 can also be secured to the first member by spot welds, adhesive, etc.

Figure 4:
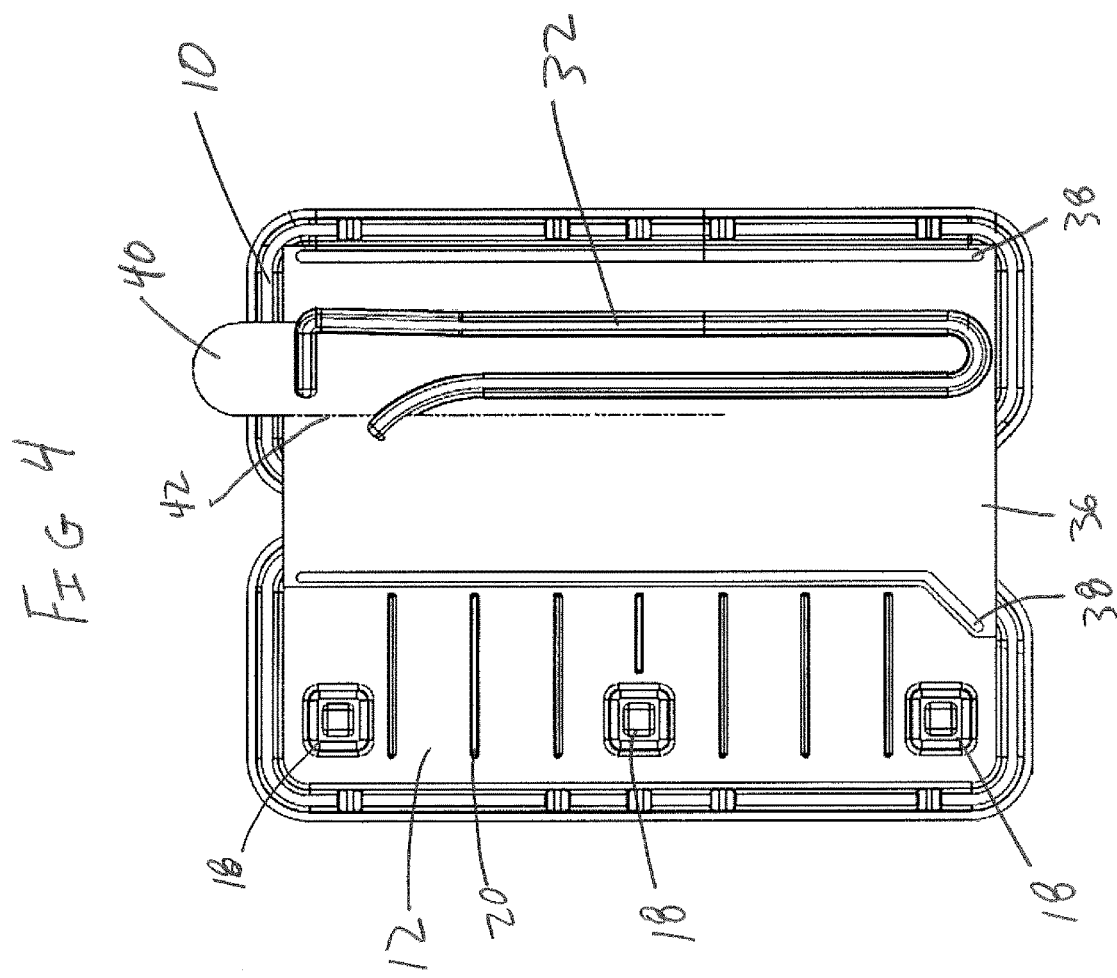
FIG. 4 illustrates a top view of a product package including the first and second members of FIG. 1 and the insert of FIG. 3.
Figure 5:
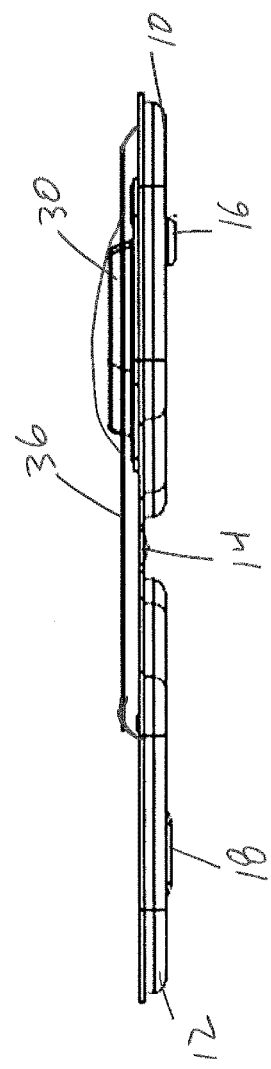
FIG. 5 illustrates a side view of the product package of FIG. 4 in a first state.

The product package also includes a flexible member 36. The flexible member 36 is connected to the proximal side 22 of the first member 10 and the first side 26 of the second member 12. The flexible member 36 shown in FIG. 4 is secured to the first and second members 10, 12 by a weld alone a weld line 38, although other methods of connecting are also contemplated. The flexible member 36 extends over the insert 30 to secure the implant in the package as explained below. A tab 40 forms a frangible connection with the flexible member. For example, a perforation 42 can be provided on the flexible member such that when the tab 40 is pulled, the flexible member is sheared at the perforation. The frangible connection could also be a reduction in thickness of the flexible member rather than a perforation to maintain any sterile barrier formed by the flexible member while still enabling shearing of the flexible member at a desired location. Removing only the portion of the flexible member defined by the tab and frangible connection can allow the product to remain in the package after opening to allow a tool to connect to the product prior to removing the product from the package.

Figure 7:
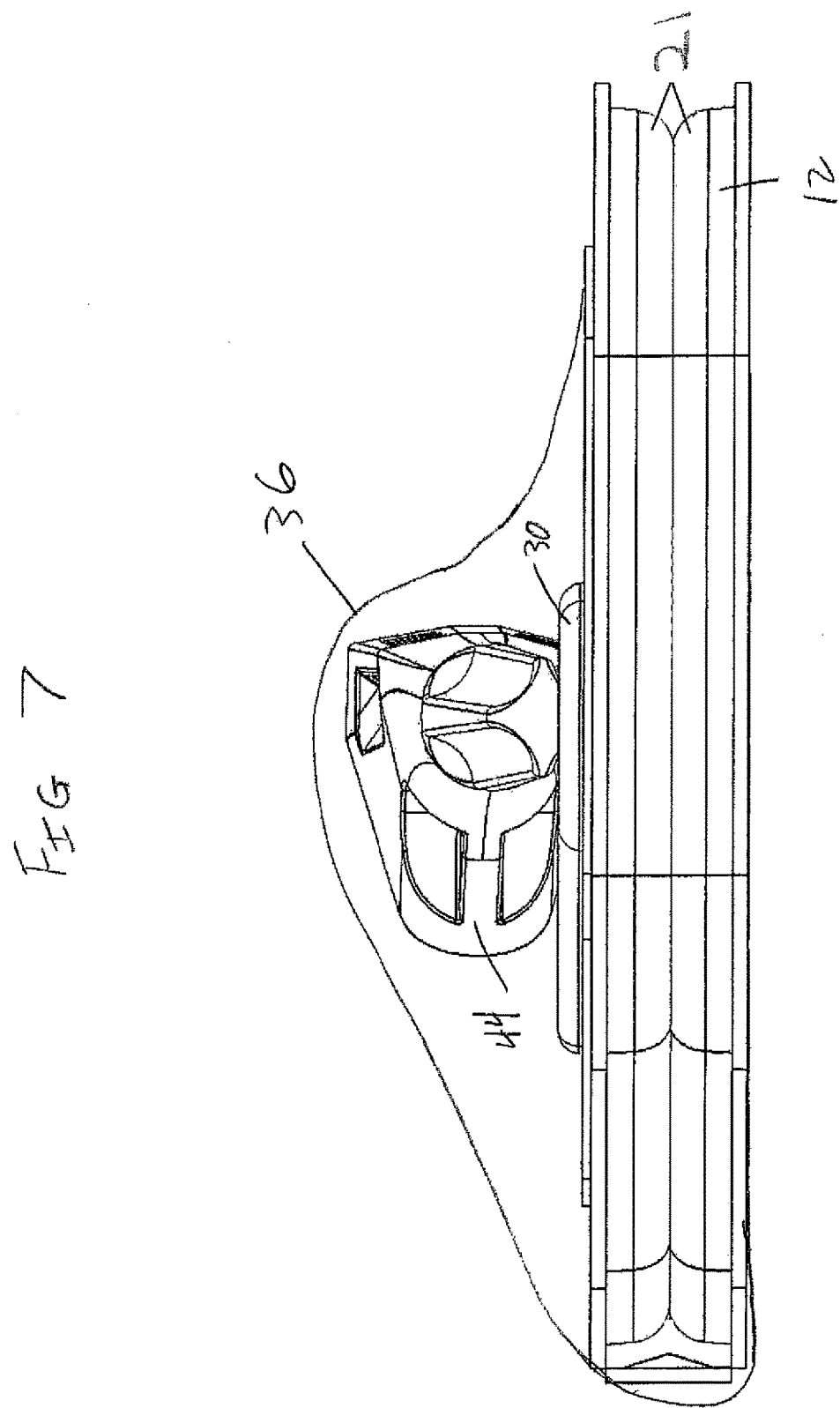
FIG. 7 illustrates a side view of the product package of FIG. 6.

FIGS. 6-7 show the package in the second state wherein the distal side 24 of the first member 10 is adjacent the second side 28 of the second member 12. An implant 44 is shown positioned in the receiving area 35 of the insert 30. The flexible member 36 (not shown in FIG. 6) extends over the implant 44 to assist in securing the implant in the package. In other words, the flexible member and the first member or insert form a pocket in which the product can be inserted. The flexible member is preferably slack when the package is in the first state (FIG. 5) such that the product can be inserted into the package before or after the flexible is coupled to the first and second members. The flexible member becomes taut as the package is transitioned to the second state (FIG. 7). The flexible member may undergo elastic or plastic deformation as the package is transitioned to the second state. A sterile barrier may be formed once the implant is in the package by further sealing the flexible member to the first and second members 10, 12. As the package is transitioned to the second state, the borders 21 of the first and second members 10, 12 may contact one another to prevent over insertion of the male connector into the female connector. Having the borders contact one another may provide additional strength to the package. In the embodiment shown in FIG. 7, the flexible member remains externally exposed when the package is in the second state.

Figure 8:
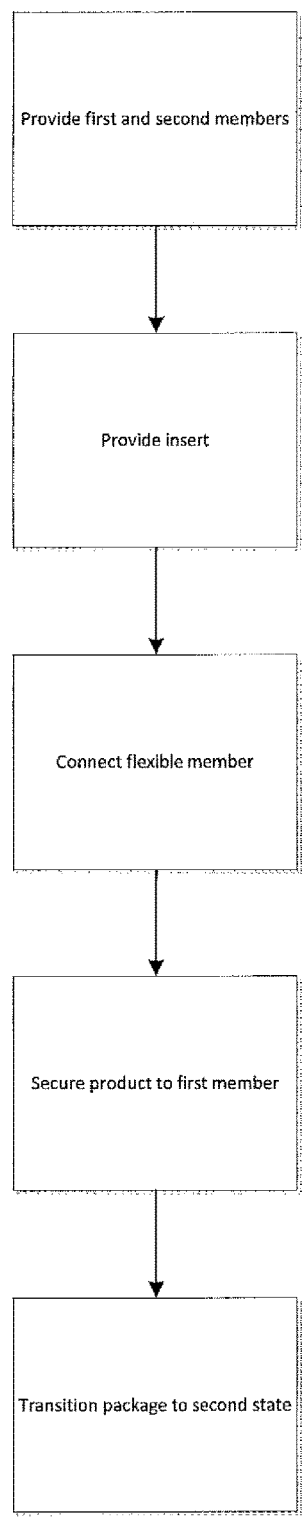
FIG. 8 is a flow chart illustrating a method of packaging a product in accordance with one embodiment of the disclosure.

A method of packaging a product is depicted in FIG. 8. The method includes providing first and second members for packaging a product. An insert configured to at least partially secure a product can optionally be connected to the proximal side of the first member. The product can be an implant.

A flexible member is connected to the proximal side of the first member and the first side of the second member before, or after, the product is secured to the first member. The product is coupled to the insert or coupled directly to the proximal side of the first member depending on whether the insert is included. Once the flexible member is connected to the first and second members, and the product is positioned between the proximal side of the first member and the flexible member, the package is transitioned from the first state to a second state. The transitioning step occurs by moving the second member with respect to the first member such that the second side of the second member is adjacent the distal side of the first member. The flexible member goes from slack to taut as the package is transitioned from the first state to the second state. The method may also include further sealing the flexible member to the first member to create a sterile barrier.

Although the invention herein has been described with reference to particular embodiments, it is to be understood that these embodiments are merely illustrative of the principles and applications of the present invention. It is therefore to be understood that numerous modifications may be made, and are encouraged to be made, to the illustrative embodiments, and that other arrangements may be devised without departing from the spirit and scope of the present invention as defined by the appended claims.

The invention claimed is:

1. An implant package, comprising:
a first member having a proximal side and a distal side;
a second member having a first side and a second side, wherein the first member includes a first border which stands proud of the distal side of the first member and the second member includes a second border which stands proud of the second side of the second member,
the first member and the second member being arrangeable in an unpackaged state and in a packaged state at which the distal side of the first member is connected to the second side of the second member, the connection in the packaged state defined by contact between the first border and the second border and by contact between a first connector on the distal side of the first member and a second connector on the second side of the second member, wherein the first border is separated from the first connector by a surface of the distal side of the first member;
a flexible member coupled to the proximal side of the first member and the first side of the second member, such that when the package is in the packaged state, the flexible member at least assists in holding an implant between the proximal side of the first member and the flexible member.

2. The implant package of claim 1, wherein the first member and the second member are rigid.

3. The implant package of claim 1, wherein the proximal side of the first member and the first side of the second member are coplanar when the implant package is in the unpackaged state.

4. The implant package of claim 1, wherein the second member is coupled to the first member by a living hinge.

5. The implant package of claim 1, wherein the flexible member has a pull tab forming a frangible connection to the flexible member.

6. The implant package of claim 1, wherein the flexible member is lax when the implant package is in the unpackaged state and is taut when the implant package is in the packaged state.

7. The implant package of claim 1, wherein the flexible member is elastically deformed when the implant package is in the packaged state.

8. The implant package of claim 1, wherein the flexible member is configured to hold is a medical device.

9. The implant package of claim 1, wherein one of the first connector and the second connector is a male element and the other of the first connector and the second connector is a female element, the first and second connectors adapted to at least assist in securing the implant package in the packaged state.

10. The implant package of claim 1, wherein the flexible member is tauter between the first member and the second member in the packaged state than in the unpackaged state.

11. An implant package comprising:

a first rigid member having a proximal side and a distal side;

a second rigid member having a first side, second side, and a border which stands proud of the second side, the second member moveable with respect to the first member to transition the implant package from an open position to a closed position;

an insert coupled to the proximal side of the first rigid member;

a flexible member over the insert and coupled to the proximal side of the first rigid member and the first side of the second rigid member; and a connector having a male element formed on one of the distal side of the first rigid member and the second side of the second rigid member and a female element formed on the other of the distal side of the first rigid member and the second side of the second rigid member to at least assist in securing the implant package in the closed position, the male or female element of the connector on the second rigid member extending from a surface of the second side to an extent different than that of the border extending from the second side.

12. The implant package of claim 11, further comprising a ridge formed on the insert adapted to at least partially secure an implant product to the insert.

13. The implant package of claim 11, wherein the flexible member is slack when the implant package is in the open position and is taut when the implant package is in the closed position.

14. The implant package of claim 11, wherein the second rigid member is coupled to the first rigid member by a living hinge.

* * * * *